United States Patent
Potterat et al.

(10) Patent No.: US 7,101,848 B2
(45) Date of Patent: Sep. 5, 2006

(54) BICYCLIC OLIGOPEPTIDES

(75) Inventors: Olivier Potterat, Mittelbiberach (DE); Ruediger Streicher, Biberach (DE); Klaus Wagner, Warthausen (DE); Till Maurer, Oberstadion (DE); Juergen Mack, Biberach (DE); Stefan Peters, Biberach (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 278 days.

(21) Appl. No.: 10/621,272

(22) Filed: Jul. 17, 2003

(65) Prior Publication Data

US 2004/0072736 A1  Apr. 15, 2004

Related U.S. Application Data

(60) Provisional application No. 60/416,797, filed on Oct. 8, 2002.

(51) Int. Cl.
*A61K 38/12* (2006.01)
(52) U.S. Cl. ....................................................... 514/10
(58) Field of Classification Search ...................... None
See application file for complete search history.

(56) References Cited

U.S. PATENT DOCUMENTS 4,139,526 A    2/1979  Veber
6,211,145 B1 *  4/2001  Yanai et al. ................... 514/10

OTHER PUBLICATIONS

Yano, et al., 1996, Bioorganic & Medicinal Chemistry, 4, 115-120.*
Renner, et al., 1999, J. Am. Chem. Sco., 121, 11273-76.*
He, et al., 1995, Bioorganic & Medicinal Chemistry, 5, 621-626.*
Janice C. Parker, et al., "Effects of Skyrin, a Receptor-Selective Glucagon Antagonist, in Rat and Human Hepatocytes", Diabetes, vol. 49, 2079-2086 Dec. 2000, XP-001154854.
James G. McCormack, et al., "Pharmacological Approaches to Inhibit Endogenous Glucose Production as a Means of Anti-diabetic Therapy", Current Pharmaceutical Design, 2001, 7, 1451-1474, XP-001154855.
K.F.Peterson, et al., "Effects of a novel glucagon receptor antagonist (Bay 27-9955) on glucagon-stimulated glucose production in humans", Diabetologia (2001) 44:2018-2024, XP-002259423.

* cited by examiner

*Primary Examiner*—Bruce R. Campell
*Assistant Examiner*—Satyanarayana R. Gudibande
(74) *Attorney, Agent, or Firm*—Michael Morris; Mary-Ellen M. Devlin; David A. Dow

(57) ABSTRACT

The invention relates to a bicyclic oligopeptide or ester thereof having the capability to inhibit the glucagon receptor, comprised of:
(a) a first cyclic group, which comprises at least one cysteine group and is formed by an amide bonding of the N-terminal amino acid with the second carboxylate group of a diacid amino acid, and
(b) a second cyclic group which is formed by an amide bonding of an amino acid with the α-carboxylate group of said diacid amino acid, and by a disulfide bonding of the C-terminal cysteine and a cysteine group within the first cyclic group (a); and
to the use of such bicyclic oligopeptides for the preparation of a medicament for the treatment or prevention of diseases, in which glucagon receptors are involved.

7 Claims, No Drawings

BICYCLIC OLIGOPEPTIDES

RELATED APPLICATIONS

Benefit of U.S. Provisional Application Ser. No. 60/416,797, filed on Oct. 8, 2002 is hereby claimed, and said Application is herein incorporated by reference.

DESCRIPTION OF THE INVENTION

The invention relates to bicyclic oligopeptides or esters thereof which have the capability to inhibit the glucagon receptor.

BACKGROUND TO THE INVENTION

The U.S. Pat. No. 5,919,926 discloses bicyclic depsipeptides which are produced by fermentation of a specific marine actinomycete (CNB-091) in saltwater-based media. These bicyclic depsipeptides are taught to be useful as anti-biotic and anti-inflammatory agents.

Glucagon is a 29-amino acid peptide hormone produced by the A-cells in the pancreas and is a major counterregulatory hormone to insulin in the maintenance of glucose homeostasis. Insulin promotes the uptake of glucose by cells, especially muscle cells and prevents an excessive breakdown of glycogen stored in liver and muscle. As an antidiabetic hormone essential for lowering blood sugar, insulin is a powerful hypoglycemic agent. In most instances, the actions of glucagon are contrary to those of insulin. Its main function is to stimulate hepatic glucose production. The activated glucagon receptor signals via the cAMP-PKA signalling cascade and increases the rate of glucose de novo synthesis via gluconeogenesis and the liberation of glucose from glycogen stores via glycogenolysis.

Diabetes is a complex disease characterized by hyperglycemia resulting from defect insulin secretion, insulin action, or both. The metabolic complications of diabetes—hyperglycemia and ketosis—are associated with a relative or absolute increase in the ratio of glucagon to insulin. Thus, glucagon is a hyperglycemic factor which causes blood sugar to increase.

Accordingly, a means of treating diabetes is to block the glucagon receptor with a suitable antagonist, thereby inhibiting glucose production by the liver and reducing glucose levels in the patient.

Several publications disclose peptidic and non-peptidic glucagon receptor antagonists (McCormick et al., Curr. Pharm. Des. 7, 1451 (2001) for review). Inhibition of glucagon-stimulated glucose production in humans has been reported for Bay 27-9955 (Petersen et al., Diabetologia 44, 2018 (2001).

It has now been surprisingly discovered that certain bicyclic oligopeptides are highly efficient inhibitors of the glucagon receptor and are therefore of potential use in the treatment or prophylaxis of hyperglycaemia and in particular in the treatment of diabetes mellitus (TypeI and TypeII).

These bicyclic oligopeptides are also indicated to be of potential use for the treatment or prophylaxis of other diseases including IGT (impaired glucose tolerance), insulin resistance syndromes, hyperinsulinemia, hyperlipidemia, dyslipidemia, arteriosclerosis, cardiovascular diseases, hypertension, cardiac hypertrophy, increased renal albumin clearance, glucagonomas, pancreatitis, obesity, gastrointestinal disorders, certain eating disorders and as a therapy to increase gastric acid secretion.

SUMMARY OF THE INVENTION

Accordingly, the invention relates to novel bicyclic oligopeptides or esters thereof having the capability to inhibit the glucagon receptor, which essentially consists of (a) a first cyclic group, which comprises at least one cysteine group and is formed by an amide bonding of the N-terminal amino acid with the second carboxylate group of a diacid amino acid, in particular the β-carboxylate group of an aspartic acid or the γ-carboxylate group of a glutamic acid, and (b) a second cyclic group which is formed by an amide bonding of an amino acid with the α-carboxylate group of said diacid amino acid, in particular aspartic or glutamic acid, and by a disulfide bonding of the C-terminal cysteine and a cysteine group within the first cyclic group (a).

Another aspect of the invention are the bicyclic oligopeptides according to the invention for the use as medicament.

Furthermore, the invention relates to a pharmaceutical composition comprising at least one bicyclic oligopeptide according to the present invention and a pharmacologically acceptable carrier and to the use of a bicyclic oligopeptide according to the present invention for the preparation of a medicament for the treatment or prevention of diseases, in which glucagon receptors are involved.

Another aspect of the invention is a method for the treatment or prevention of diseases, in which glucagon receptors are involved, which method comprises administration of an effective amount of a bicyclic oligopeptide according to the present invention to a patient in need thereof.

DETAILED DESCRIPTION OF THE INVENTION

The term "second carboxylate group" as used hereinbefore and hereinbelow with respect to a diacid amino acid relates to the carboxylate group which is not attached to the carbon atom which bears the amino group. Preferably it relates to the β- or γ-carboxylate group of an aspartic or glutamic acid.

The term "diacid amino acid" as used hereinbefore and hereinbelow with respect to a the amino acid which forms the first cyclus with the N-terminal amino acid via an amide bond relates to an amino acid which exhibits two carboxylate groups, preferably aspartic or glutamic acid.

In a preferred embodiment the invention relates to a bicyclic oligopeptide, which comprises at least 3 amino acid moieties between the N-terminal amino acid and the said diacid amino acid; and/or which comprises at least 4 amino acid moieties between the said diacid amino acid and the C-terminal cysteine.

Furthermore preferred are such bicyclic oligopeptides, which are obtainable by isolation from an *Actinomyces*, preferably a *Streptomyces* sp., in particular the microorganism which is deposited pursuant to the Budapest Treaty under the accession number DSM 14996, and optionally derivatized subsequently by esterification.

Preferably, the *Streptomyces* sp. are cultured in a medium comprising soy flour, glucose, sodium chloride, $CaCO_3$, $KH_2PO_4$, glucose-casein pepton, yeast extract, meat extract and water at a pH-value from 6.5 to 7.5, in particular from 6.8 to 7.3 at temperatures from 25 to 35° C., in particular at about 28° C.

The bicyclic oligopeptide is preferably obtainable from said fermentation broth by extraction with a polar organic solvent, preferably an alcohol such as methanol and ethanol or dimethylsulfoxide (DMSO) or mixtures thereof, most preferably a mixture of methanol and DMSO, wherein the methanol to DMSO ratio ranges from 1000:1 to 10:1, in particular from 500:1 to 100:1. The extract is preferably concentrated in vacuo and the concentrated extract is enriched by chromatography, in particular by preparative HPLC using acetonitrile and ammonium acetate buffer (pH 3–5), in particular in form of a gradient of 2–60% of acetonitrile and ammonium acetate buffer, as eluent. The enriched product is preferably purified by column chromatography using an alcohol, preferably methanol as eluent.

The optional esterification is carried out using standard esterification methods, preferably by reaction of the bicyclic oligopeptide with trimethylsilyldiazomethane, in particular in form of a 2N solution in hexane in a polar organic solvent, preferably acetonitrile or methanol or a mixture thereof. The reaction mixture is preferably purified by preparative HPLC and freeze dried.

Particularly preferred are bicyclic oligopeptides, which are characterized by formula I,

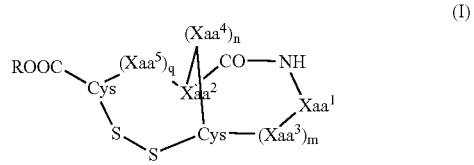

(I)

wherein

Xaa$^1$ represents a N-terminal α-amino acid, in particular selected from the group consisting of glycine, alanine, leucine, norleucin and valine, in particular glycine;

Xaa$^2$ represents a diacid amino acid, preferably an aspartic or glutamic acid, in particular aspartic acid, Xaa$^3$, Xaa$^4$ and Xaa$^5$ each independently represent an α-amino acid, preferably selected from the group consisting of glycine, alanine, isoleucine, leucine, norleucine, valine, proline, threonine, asparagine, tryptophan and serine m, n and q each independently represent an integer from 2 to 12, preferably wherein the sum of m+n+q is an integer from 11 to 22, in particular from 13 to 17; and R represents a hydrogen atom or a C$_{1-6}$ alkyl group.

Most particularly preferred are the compounds of formula I, wherein

Xaa$^3$ each independently represent an α-amino acid selected from the group consisting of glycine, alanine, leucine, norleucine, valine, proline and tryptophan, in particular glycine, leucine, proline and tryptophan;

Xaa$^4$ each independently represent an α-amino acid selected from the group consisting of glycine, alanine, leucine, norleucine, valine, proline and serine, in particular proline and serine; and Xaa$^5$ each independently represent an α-amino acid selected from the group consisting of glycine, alanine, isoleucine, leucine, norleucine, valine, proline, threonine, asparagine, tryptophan and serine, in particular glycine, alanine, isoleucine, proline, threonine, asparagine, tryptophan and serine, m represents an integer from 3 to 6, in particular 4;

n represents an integer from 2 to 4, in particular 2;

q represents an integer from 6 to 12, in particular 9; and

R represents a hydrogen atom or a methyl group.

Most preferred is a bicyclic nonadecapeptide or ester thereof, characterized by the following sequence (SEQ ID NO. 1):

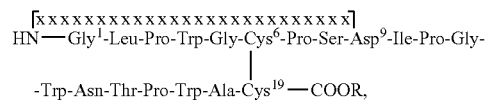

wherein the amino group of Gly$^1$ is linked with the β-carboxylate group of Asp$^9$ via an amide group, the thiole groups of the cysteines Cys$^6$ and Cys$^{19}$ are linked via a disulfide bridge, and R is a hydrogen atom or a methyl group.

In addition to the method to isolate the bicyclic oligopeptides from *Streptomyces* sp., the compounds of the present invention can be synthetically prepared from amino acids applying standard solid phase peptide synthesis.

The polymer matrix can be selected from commercially available sources, preferably polystyrene, polyethylene glycol, or polyacrylamide resins.

The linker is selected in the way that upon cleavage from the resin the peptide is liberated containing a caboxylic acid at the C-terminus. Therefore, preferably the so called 2-chlorotrityl-resin bearing a 2-chlorotrityl linker or the so called Wang-resin containing the 4-hydroxymethylphenoxybenzyl-linker, which are both commercially available, are applicable. Due to known side reactions in peptide synthesis with C-terminal cysteine residues like diketopiperazine formation it is recommended to start with commercially available H-Cys(Acm)-2-chlorotrityl resin (Nova Biochem).

The stepwise peptide assembly is preferably performed under standard conditions using Nα-Fmoc-protected (PG1) amino acids and in situ activation reagents like TBTU. The side chains in the amino acids are protected as usual for Fmoc/tBu-peptide synthesis, e.g. tBu for serine and threonine, trityl for asparagine, Boc for tryptophan (PG2).

The cysteine residues should be protected by protecting groups, which can be selectively removed at the end of the synthesis. For this purpose preferably the acetamidomethyl (ACM) group (PG3) which is stable towards TFA is selected.

For the on-resin cyclisation of the diacid amino acid, in particular Asp and the N-terminal amino acid, in particular Gly, the side chain carboxylic acid of the diacid amino acid, in particular aspartic acid need to be selectively deprotected without cleaving the peptide from the solid support. Therefore, an allylester protecting group is most suitable.

The peptide assembly is as a rule performed under standard conditions until completion of the coupling of the N-terminal Fmoc-protected amino acid, in particular Fmoc-glycine residue. For the cyclisation of N-terminal amino acid, in particular glycine-1 and the diacid amino acid, in particular aspartic or glutaric acid it is necessary to deprotect the amino and the acid function of both amino acids, respectively. The allylester of aspartic or glutaric acid can be cleaved applying palladium catalysts, preferably Pd(PPh$_3$)$_4$ in presence of a nucleophile, preferably dimedone, barbituric acid or dimethylamine. The Fmoc-group of the N-terminal group, in particular glycine can be removed as a rule with 20% piperidine in DMF. The ring formation can be achieved with standard peptide coupling reagents, preferably TBTU.

The cleavage of the peptide from the polymer can be performed with trifluoroacetic acid (TFA), preferably 50% TFA in dichloromethane. Using these conditions, the trityl-, tBu- and Boc-protecting groups in the peptide are also removed. At this stage, it is recommended to purify the peptide by reversed phase HPLC. The deprotection of the cysteine residues and disulfide formation is preferably carried out with mercury(II)-salts, preferably mercury(II)-acetate, or iodine. The following reaction scheme (SEQ ID NO. 2–5) illustrates the solid phase peptide synthesis of the bicyclic oligopeptide according to the present invention:

Usually the pharmaceutical compositions of the present invention will be adapted for oral administration, although compositions for administration by other routes, such as by injection and percutaneous absorption are also envisaged.

Particularly suitable compositions for oral administration are unit dosage forms such as tablets and capsules. Other fixed unit dosage forms, such as powders presented in sachets, may also be used.

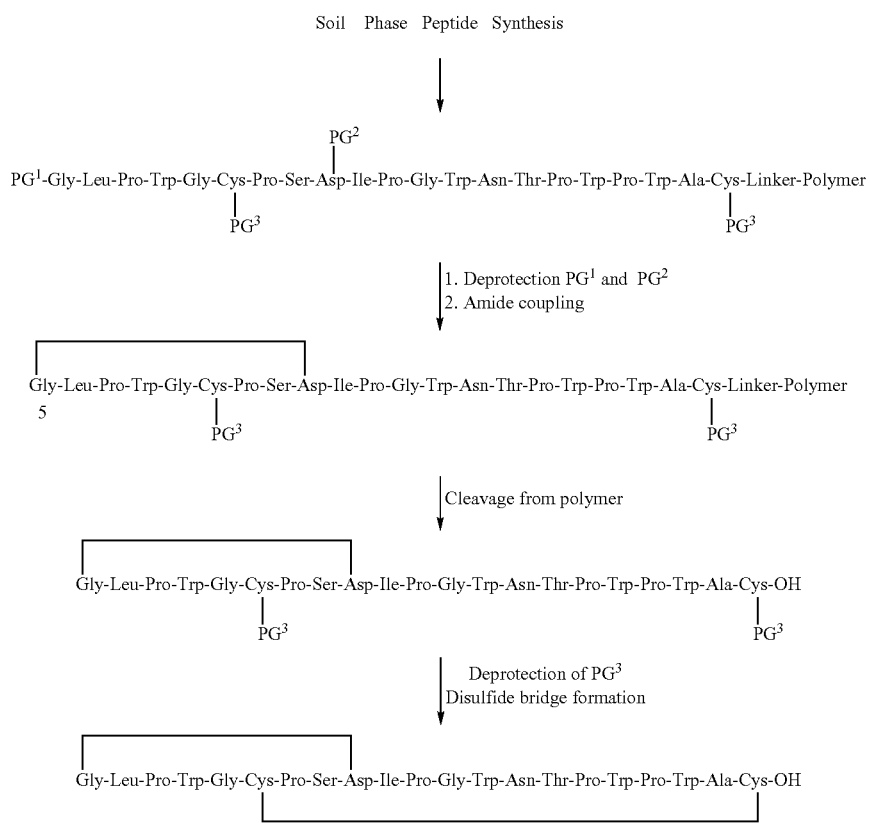

As indicated hereinbefore the present invention also provides a bicyclic oligopeptide or an ester thereof and/or a pharmaceutically acceptable salt thereof and/or a pharmaceutically acceptable solvate thereof for use in the treatment of hyperglycaemia, hyperlipidaemia, hypertension, cardiovascular diseases and certain eating disorders.

A bicyclic oligopeptide or an ester thereof and/or a pharmaceutically acceptable salt thereof and/or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising a bicyclic oligopeptide or an ester thereof, or a pharmaceutically acceptable salt thereof, or a pharmaceutically acceptable solvate thereof, and a pharmaceutically acceptable carrier therefor.

As used herein the term 'pharmaceutically acceptable' embraces compounds, compositions and ingredients for both human and veterinary use: for example the term 'pharmaceutically acceptable salt' embraces a veterinarily acceptable salt.

The composition may, if desired, be in the form of a pack accompanied by written or printed instructions for use.

In accordance with conventional pharmaceutical practice the carrier may comprise a diluent, filler, disintegrant, wetting agent, lubricant, colourant, flavourant or other conventional adjuvant.

Typical carriers include, for example, microcrystalline cellulose, starch, sodium starch glycollate, polyvinylpyrrolidone, polyvinylpolypyrrolidone, magnesium stearate, sodium lauryl sulphate or sucrose.

Most suitably the composition will be formulated in unit dose form. Such unit dose will normally contain an amount of the active ingredient in the range of from 0.01 to 1000 mg, more usually 0.1 to 500 mg, and more especially 0.1 to 250 mg.

The present invention further provides a method for the treatment and/or prophylaxis of hyperglycaemia in a human or non-human mammal which comprises administering an effective, non-toxic, amount of a compound of the bicyclic oligopeptide or the ester thereof and/or a pharmaceutically acceptable salt thereof and/or a pharmaceutically acceptable solvate thereof to a hyperglycaemic human or non-human mammal in need thereof.

The present invention further provides a method for the treatment of hyperlipidaemia in a human or non-human mammal, which comprises administering an effective, non-toxic, amount of a bicyclic oligopeptide or an ester thereof and/or a pharmaceutically acceptable salt thereof and/or a pharmaceutically acceptable solvate thereof, to a hyperlipidaemic human or non-human mammal in need thereof.

Conveniently, the active ingredient may be administered as a pharmaceutical composition hereinbefore defined, and this forms a particular aspect of the present invention.

In the treatment and/or prophylaxis of hyperglycaemic humans, and/or the treatment and/or prophylaxis of hyperlipidaemic human, the bicyclic oligopeptide or the ester thereof and/or a pharmaceutically acceptable salt thereof and/or a pharmaceutically acceptable solvate thereof, may be taken in doses, such as those described above, one to six times a day in a manner such that the total daily dose for a 70 kg adult will generally be in the range of from 0.1 to 6000 mg, and more usually about 1 to 1500 mg.

In the treatment and/or prophylaxis of hyperglycaemic non-human mammals, especially dogs, the active ingredient may be adminstered by mouth, usually once or twice a day and in an amount in the range of from about 0.025 mg/kg to 25 mg/kg, for example 0.1 mg/kg to 20 mg/kg. Similar dosage regimens are suitable for the treatment and/or prophylaxis of hyperlipidaemia in non-human mammals.

The bicyclic oligopeptide or the ester thereof may be administered alone or in combination with another active agent, which is conventionally used in the treatment or prophylaxis of hyperglycaemia, hyperlipidemia, obesity and hypertension.

In particular the compounds according to the invention may be used in combination with one or more antidiabetic agents. The antidiabetic agents comprise biguanides, glucosidase inhibitors, PPARgamma modulators, dual PPARalpha/gamma agonists, RXR modulators, SGLT2 inhibitors, aP2 inhibitors, insulin sensitizers, GLP-1 or mimetics, DPPIV inhibitors, PTP-1B inhibitors, GSK-3 inhibitors and/or a metiglinide. The antidiabetic agent is specifically metformin, glyburide, glibenclamide, glimepiride, glypiride, glipizide, chlorpropamide, gliclazide, acarbose, miglitol, pioglitazone, troglitazone, rosiglitazone, insulin, isaglitazone, repaglinide, nateglinide, and/or exendin-4.

The compounds of the invention may be used in combination with lipid modulating agents. The lipid modulating agents comprise HMG CoA reductase inhibitors, fibric acid derivatives, CETP inhibitors, ACAT inhibitors, MTP inhibitors, squalene cyclase and squalene synthetase inhibitors, LXR modulators and/or bile acid sequestrants. The lipid modulating agent is especially pravastatin, lovastatin, fluvastatin, simvastatin, atorvastatin, rosuvastatin, fenofibrate, gemfibrozil, clofibrate, cholestyramine, colestipol, probucol, nicotinic acid, implitapide and/or avasimibe.

The compounds of the invention may be used in combination with anti-obesity agents. The anti-obesity agents comprise lipase inhibitors, serotonin and dopamine reuptake inhibitors, beta3 adrenergic agonists, MCH antagonists, MC4 agonists, leptin or mimetics, fatty acid oxidation upregulators and/or fatty acid and triglyceride synthesis inhibitors. The anti-obesity agent is especially orlistat, sibutramine, topiramate, axokine, dexamphetamine, phentermine, phenylpropanolamine, famoxin and/or mazindol.

The compounds of the invention may be used in combination with cardiovascular agents. The cardiovascular agents comprise alpha-adrenergic blockers, angiotensin converting enzyme inhibitors, angiotensin II receptor blockers, antiarrhytmic agents, anticoagulants, antiplatelet agents, thrombolytic agents, beta-adrenergic blockers, calcium antagonists, centrally acting hypertensive agents, diuretics, neuronal and ganglionic blockers, and/or vasodilators. The cardiovascular agent is specifically doxazosin, prazosin, terazosin, benazepril, captopril, enalapril, enalaprilat, fosinopril, lisinopril, moexipril, quinapril, ramipril, trandolapril, irbesartan, losartan, valsartan, telmisartan, disopyramide, flecainide, ibutilide, lidocaine, mexiletine, moricizine, procainamide, propafenone, quinidine, tocainide, amiodaron, bretylium, anisindione, dicumarol, heparin, warfarin, abciximab, anagrelide, aspirin, clopidogrel, dipyridamole, ticlopidine, alteplase, anistreplase, reteplase, streptokinase, urokinase, nadolol, propanolol, sotalol, timolol, atenolol, betaxolol, bisoprolol, esmolol, metoprolol, acebutolol, carteolol, penbutolol, pindolol, carvedilol, labetalol, amlodipine, bepridil, diltiazem, felodipine, isradipine, mibefradil, nicardipine, nifedipine, nimodipine, verapamil, clonidine, guanabenz, guanfacine, methyldopa, bumetanide, ethacrynic acid, furosemide, torsemide, bendroflumethiazide, benthiazide, chlorothiazide, chlorthalidone, hydrochlorothiazide, hydroflumethiazide, methyclothiazide, metolazone, polythiazide, quinethazone, trichlormethiazide, amiloride, spironolactone, guanadrel, guanethidine, mecamylamine, reserpine, cyclandelate, fenoldopam, hydralazine, minoxidil, pentoxifylline, phenoxybenzamine, erythrityl tetranitrate, isosorbide, nitroglycerin, and/or nitroprusside.

The dosages regimens for the treatment of other diseases (e.g. hypertension, cardiovascular disease and eating disorders) will generally be those mentioned above in relation to hyperglycaemia.

In a further aspect the present invention provides the use of a bicyclic oligopeptide or an ester thereof and/or a pharmaceutically acceptable salt thereof and/or a pharmaceutically acceptable solvate thereof, for the manufacture of a medicament for the treatment and/or prophylaxis of hyperglycaemia.

The present invention also provides the use of a bicyclic oligopeptide or an ester thereof and/or a pharmaceutically acceptable salt thereof, and/or a pharmaceutically acceptable solvate thereof, for the manufacture of a medicament for the treatment and/or prophylaxis of hyperlipidaemia, hypertension, cardiovascular disease or certain eating disorders.

A major advantage of the bicyclic oligopeptide according to the invention is its high glucagon receptor affinity and its surprising stability in physiological media.

The examples that follow serve to illustrate the present invention. They are to be understood as being merely illustrative given solely as examples without restricting the invention to their content.

EXAMPLE 1

Preparation and Isolation of Bicyclic Nonadecapeptid of the Following Sequence (SEQ ID NO. 5):

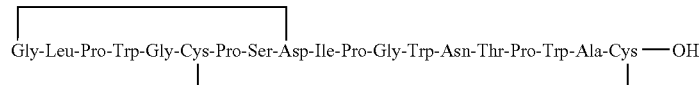

1. Preparation (a) Pre-Culture:

100 mL of the following culture medium are prepared in 300 ml Erlenmeyer flasks with 4 chicanes:

soy flour 15.0 g, glucose 15.0 g, sodium chloride 5.0 g, CaCO$_3$ 1.0 g, KH$_2$PO$_4$ 0.3 g and water ad 1000 ml, pH 6.9. A small slice of agar with a well cultivated stem of streptomycetes DSM 14996 serves as inoculum. The flasks are agitated 48 hours at 160 U/min and 28° C.

(b) Fermentation 250 ml of a glucose-casein pepton medium are prepared in 1L Erlenmeyer flasks:

Glucose 20.0 g, casein pepton 4.0 g, yeast extract 0.5 g, meat extract 4.0 g, sodium chloride 2.5 g, CaCO$_3$ 3.0 g, water ad 1000 ml, pH 7.2. Each of the flasks is inoculated with 20 ml of the pre-culture and maintained 120 Std. at 160 U/min and 28° C.

2. Isolation:

(a) Extraction

The mycelia and the lyophilisate from 6 L culture broth are combined and extracted with a mixture of MeOH (2l and 1l) and DMSO (2×5 ml) twice. The extract is concentrated to a remaining volume of about 40 ml (extract A) in vacuo. The precipitate thereof is centrifuged off and dissolved in a mixture of MeOH (6 ml) and DMSO (3 ml), which is added to the concentrated extract (extract A).

(b) Chromatography

The resulting extract A is purified by preparative HPLC in portions of 1.8 ml with a C-18 Nova-Pack column (Waters, 6 μm, 2.5×10 cm) with pre-column (2.5×1.0 cm). A gradient of 5–51% CH$_3$CN against 1 mM ammonium acetate buffer (pH 4) within 16 min serves as eluant. The flow rate is 20 ml/min. The peptide is detected by UV absorption at 220 nm. Subsequently, the enriched peptide is purified on a Sephadex LH-20 column (2.5×70 cm) in portions of 100 mg using MeOH (1.0 m/min) as eluent, to yield 25 mg/L of the pure desired product.

EXAMPLE 2

Esterification of the Compound of Example 1

A mixture of trimethylsilyldiazomethane (2N solution in hexane, 0.048 ml, 0.096 mmol) and acetonitril/methanol (9/1, 0.85 ml) is added to a mixture of the bicyclic nonadecapeptide prepared in example 1 (23.7 mg, 0.0116 mmol) and 0.85 ml DMSO. After 20 h another portion of trimethylsilyldiazomethane (2N solution in hexane, 0.048 ml, 0.096 mmol) is added. The reaction is then controlled by LC-MS indicating that 75% of the acid (retention time=5.84 min, (M−H)−:2035, (M−2H)2−:1017) has been converted to the methyl ester (retention time=5.96 min, (M+H)+:2051, (M+2H)2+:1026). The reaction mixture is purified by preparative HPLC and freeze dried.

The compounds of examples 1 and 2 show the following properties:

| Example 1: C95H125N23O24S2 | MW2035.87 (monoisotopic) |
| | 2037.3 (average) |
| Example 2: C96H127N23O24S2 | MW2049.89 (monoisotopic) |
| | 2051.3 (average) | and the following solubilities:

| Example 1 | |
| --- | --- |
| Buffer pH 3.0: | 0.003 mg/ml |
| Buffer pH 7.4: | 0.120 mg/ml |
| Buffer pH 10.0: | 0.092 mg/ml |
| Example 2 | |
| Buffer pH 3.0: | 0.003 mg/ml |
| Buffer pH 7.4: | 0.002 mg/ml |
| Buffer pH 10.0: | 0.004 mg/ml |

EXAMPLE 3

Glucagon Binding Assay

Binding of peptides to the glucagon receptor was assayed in a competition binding-assay using a membrane fraction containing the cloned human glucagon receptor and radiolabeled glucagon.

The cDNA coding for the human glucagon receptor was cloned into expression vector pcDNA3.1 (Invitrogene). Baby hamster kidney cells (BHK-21(C-13) cells (ATCC)) were transfected with the expression construct for the human glucagon receptor and a stably transfected cell clone was isolated after selection with G-418 (Gibco).

Plasma membranes containing the human glucagon receptor were prepared from stably transfected BHK-21 cells. Cells were grown to confluence, washed and detached with ice cold PBS buffer (Gibco), containing 0.05% EDTA and collected in PBS buffer. The cells were collected by centrifugation and suspended in 20 volumes of ice-cold tris buffer (10 mM tris/HCl, pH7.2; 0.01 mM PMSF (Phenylmethylsulfonyl fluoride)) and incubated for 90 minutes. All further steps were performed at 4° C. The suspension was lysed completely by 10 strokes of a Dounce homogenizer. Nuclei and cellular debris were separated by centrifugation for 10 min. at 500 g. The supernatant was then centrifuged at 100,000 g for 35 minutes. The precipitated membranes were suspended in incubation buffer (50 mM tris/HCl, 100 mM NaCl, 5 mM MgCl2, 1 mM EDTA, 0.2% bovine serum albumin, pH 7.2), aliquoted and stored at −80° C.

After thawing BHK cell membranes expressing the human glucagon receptor were re-suspended in incubation buffer completed with 0.01 mM PMSF.

For measuring competition with glucagon binding, 20 μg of the membrane suspension were incubated for 60 minutes in covered microtiter plates (Optiplate, Packard Instruments) with 50.000 cpm 125I-glucagon (Amersham Pharmacia), and one concentration of the test compound in a total volume of 100 μl. The protein-bound radioactivity is separated from unbound ligand by filtration and washing on a Multiscreen-Vakuumfiltrationsystem (Millipore) using GC/B filters (Packard) and measured after addition of 20 μl Microscint 20 in a topcount scintillation counter (Packard). The non-specific binding is defined as radioactivity bound in the presence of 1 μM glucagon (Wherl GmbH).

Accordingly an $IC_{50}$ value can be calculated from the results obtained in the above test method. The bicyclic oligopeptides show the following activities:

Example 1: $IC_{50}$=100 nM;
Example 2: $IC_{50}$=135 nM;

EXAMPLE 4

Metabolic Stability:

Incubations with preparations of microsomes and cytosol and with plasma under conditions as described below are suitable to investigate the metabolic stability of test compounds (e.g. oxidative metabolism reactions and hydrolysis by esterases). The metabolic stability of the test compounds of examples 1 and 2 is investigated in liver microsomes and cytosol of humans, dogs and rats and in plasma of humans and rats.

Stability with Microsomes and Cytosol

Incubations of test compounds (final concentration: 1 μM) are performed with liver microsomes and cytosol (0.5 mg protein/ml) in Tris buffer (Tris-(hydroxymethyl)-aminomethane) pH 7.4 (0.1 M) containing magnesium chloride (5 mM) at 37° C. for up to 45 min in a total volume of 100 μl. The reaction is initiated by addition of β-nicotinamide adenine dinucleotide phosphate, reduced form (NADPH, 1 mM) and terminated by addition of acetonitrile. After vortex mixing and centrifugation the supernatants are analyzed.

Stability in Plasma

Incubations of test substrates (final concentration: 1 μM) are performed with human and rat plasma (heparin) containing 0.1 M Tris buffer pH 7.4. The reaction is initiated by addition of the test compound at 37° C. for up to 45 min and terminated by addition of acetonitrile. After vortex mixing and centrifugation the supernatants are analyzed.

Analytic

The samples are analyzed by on-line solid phase extraction and reversed phase HPLC coupled to electro-spray ionization tandem mass spectrometry. The measurements are performed on a triple quad mass spectrometer Quattro II (Micromass, Manchester, UK). The instrument operates at nominal mass resolution in SIR-mode. The analytes are quantified by detection of their quasimolecular ions $[M+2H]^{2+}$ m/z 1019 (Example 1) and m/z 1026 (Example 2).

The following stabilities are obtained

Substrate (initial conc.): 1 μM
Half-lives, (t½ [min])

| Species | Rat | | | Dog | | Human | | |
|---|---|---|---|---|---|---|---|---|
| | Micros | Cytosol | Plasma | Micros | Cytosol | Micros | Cytosol | Plasma |
| Example 1 | stable | stable | stable | stable | stable | stable | stable | 182 |
| Example 2 | stable | 73 | stable | stable | 140 | stable | 122 | 180 |

EXAMPLE 5

Examples of pharmaceutical formulations

A) Tablets — per tablet

| | |
|---|---|
| active substance (Example 1) | 50 mg |
| lactose | 170 mg |
| corn starch | 260 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

B) Tablets — per tablet

| | |
|---|---|
| active substance (Example 1) | 40 mg |
| corn starch | 210 mg |
| lactose | 65 mg |
| microcrystalline cellulose | 40 mg |
| polyvinylpyrrolidone | 20 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened.

The sodium-carboxymethyl starch and the magnesium stearate are added and mixed in and the mixture is compressed to form tablets of a suitable size.

C) Coated tablets — per coated tablet

| | |
|---|---|
| Active substance (Example 1) | 5 mg |
| Corn starch | 41.5 mg |

| C) | Coated tablets | per coated tablet |
|---|---|---|
| | Lactose | 30 mg |
| | Polyvinylpyrrolidone | 3 mg |
| | Magnesium stearate | 0.5 mg |
| | | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

| D) | Capsules | per capsule |
|---|---|---|
| | Active substance (Example 1) | 25 mg |
| | Corn starch | 283.5 mg |
| | Magnesium stearate | 1.5 mg |
| | | 310 mg |

The substance and corn starch are mixed and moistened with water. The moist mass is screened and dried. The dry granules are screened and mixed with magnesium stearate. The finished mixture is packed into size 1 hard gelatine capsules.

| E) | Ampoule solution | |
|---|---|---|
| | active substance (Example 1) | 0,5 mg |
| | sodium chloride | 50 mg |
| | water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which 0 are then sterilised and sealed by fusion. The ampoules contain 0.5 mg, 2.5 mg and 5.0 mg of active substance.

| F) | Suppositories | |
|---|---|---|
| | Active substance (Example 2) | 30 mg |
| | Solid fat | 1670 mg |
| | | 1700 mg |

The solid fat is melted. The ground active substance is homogeneously dispersed at 40° C. It is cooled to 38° C. and poured into slightly chilled suppository moulds.

What is claimed is:

1. An isolated or synthesized bicyclic oligopeptide $$\text{HN}-\text{Gly}^1\text{-Leu-Pro-Trp-Gly-Cys}^6\text{-Pro-Ser-Asp}^9\text{-Ile-Pro-Gly-} \\ | \\ \text{-Trp-Asn-Thr-Pro-Trp-Ala-Cys}^{19}-\text{COOR},$$

comprised of (SEQ ID NO. 1):
wherein
the amino group of $Gly^1$ is linked with the β-carboxylate group of $Asp^9$ via an amide group, and the thiol groups of the cysteines $Cys^6$ and $Cys^{19}$ are linked via a disulfide bridge and R is a H atom or a methyl group; or an ester thereof.

2. A medicament comprised of a bicyclic oligopeptide according to claim 1.

3. A Pharmaceutical composition comprising a bicyclic oligopeptide according to claim 1 and a pharmacologically acceptable carrier.

4. A pharmaceutical composition according to claim 3 further comprised of an active ingredient selected from the group consisting of antidiabetic agents, lipid modulating agents, anti-obesity agents and cardiovascular agents.

5. A pharmaceutical composition according to claim 4, wherein the antidiabetic agent is selected from the group consisting of biguanides, glucosidase inhibitors, PPAR-gamma modulators, dual PPARalpha/gamma agonists, RXR modulators, SGLT2 inhibitors, aP2 inhibitors, insulin sensitizers, GLP-I or mimetics, DPPIV inhibitors, PTP-IB inhibitors, GSK-3 inhibitors and a metiglinide.

6. A Pharmaceutical composition according to claim 4 wherein the antidiabetic agent is selected from the group consisting of metformin, glyburide, glibenclamide, glimepiride, glypiride, glipizide, chlopropamide, gliclazide, acarbose, miglitol, pioglitazone, troglitazone, rosiglitazone, insulin, isaglitazone, repaglinide, nateglinide, and exendin-4.

7. A method of treating diabetes mellitus comprising the step of administering to a patient in need thereof a therapeutically effective amount of a bicyclic oligopeptide according to claim 1.

* * * * *

SEQUENCE LISTING

```
<160> NUMBER OF SEQ ID NOS: 5
<210> SEQ ID NO 1
<211> LENGTH: 19
<212> TYPE: PRT
<213> ORGANISM: Artificial Sequence
<220> FEATURE:
<223> OTHER INFORMATION: bicyclic nonadecapeptide or ester thereof
<220> FEATURE:
<221> NAME/KEY: BINDING
<222> LOCATION: 1
<223> OTHER INFORMATION: amino acid 1 (Gly) is attached by HN
<220> FEATURE:
<221> NAME/KEY: BINDING
<222> LOCATION: 1
<223> OTHER INFORMATION: amino acid 1 (Gly) is linked with the
      beta-carboxylate group of Asp via an amide group
<220> FEATURE:
<221> NAME/KEY: BINDING
<222> LOCATION: 6,19
<223> OTHER INFORMATION: aminio acids 6 & 19 (Cys) are the thiole groups
      of cysteines and are linked via a disulfide bridge
<220> FEATURE:
<221> NAME/KEY: BINDING
<222> LOCATION: 19
<223> OTHER INFORMATION: amino acid 19 (Cys) is attached by COOR

<400> SEQUENCE: 1

Gly Leu Pro Trp Gly Cys Pro Ser Asp Ile Pro Gly Trp Asn Thr Pro
1               5                   10                  15

Trp Ala Cys
```

```
<210> SEQ ID NO 2
<211> LENGTH: 19
<212> TYPE: PRT
<213> ORGANISM: Artificial Sequence
<220> FEATURE:
<223> OTHER INFORMATION: solide phase peptide synthesis
<220> FEATURE:
<221> NAME/KEY: BINDING
<222> LOCATION: 1
<223> OTHER INFORMATION: amino acid 1 (Gly) is attached by PG1 (N
      alpha-Fmoc-protected)
<220> FEATURE:
<221> NAME/KEY: BINDING
<222> LOCATION: 6,19
<223> OTHER INFORMATION: amino acids 6 & 19 (Cys) are attached by PG3
      (acetamidomethyl (ACM0 group)
<220> FEATURE:
<221> NAME/KEY: BINDING
<222> LOCATION: 9
<223> OTHER INFORMATION: amino acid 9 (Asp) is attached by PG2 (Boc for
      tryptophan)
<220> FEATURE:
<221> NAME/KEY: BINDING
<222> LOCATION: 19
<223> OTHER INFORMATION: amino acid 19 (Cys) is attached to Linker-
      Polymer

<400> SEQUENCE: 2

Gly Leu Pro Trp Gly Cys Pro Ser Asp Ile Pro Gly Trp Asn Thr Pro
 1               5                   10                  15

Trp Ala Cys

<210> SEQ ID NO 3
<211> LENGTH: 19
<212> TYPE: PRT
<213> ORGANISM: Artificial Sequence
<220> FEATURE:
<223> OTHER INFORMATION: solide phase peptide synthesis
<220> FEATURE:
<221> NAME/KEY: BINDING
<222> LOCATION: 6,19
<223> OTHER INFORMATION: amino acids 6 & 19 (Cys) are attached by PG3
      (acetamidomethyl (ACM) group)
<220> FEATURE:
<221> NAME/KEY: BINDING
<222> LOCATION: 19
<223> OTHER INFORMATION: amino acid 19 (Cys) is attached by a
      Linker-Polymer

<400> SEQUENCE: 3

Gly Leu Pro Trp Gly Cys Pro Ser Asp Ile Pro Gly Trp Asn Thr Pro
 1               5                   10                  15

Trp Ala Cys

<210> SEQ ID NO 4
<211> LENGTH: 19
<212> TYPE: PRT
<213> ORGANISM: Artificial Sequence
<220> FEATURE:
<223> OTHER INFORMATION: solide phase peptide synthesis
<220> FEATURE:
<221> NAME/KEY: BINDING
<222> LOCATION: 6,19
<223> OTHER INFORMATION: amino acids 6 & 19 (Cys) are attached by PG3
      (acetamidomethyl (ACM) group)
<220> FEATURE:
<221> NAME/KEY: BINDING
<222> LOCATION: 19
<223> OTHER INFORMATION: amino acid 19 (Cys) is attached by OH

<400> SEQUENCE: 4
```

```
-continued

Gly Leu Pro Trp Gly Cys Pro Ser Asp Ile Pro Gly Trp Asn Thr Pro
 1               5                  10                  15

Trp Ala Cys

<210> SEQ ID NO 5
<211> LENGTH: 19
<212> TYPE: PRT
<213> ORGANISM: Artificial Sequence
<220> FEATURE:
<223> OTHER INFORMATION: solide phase peptide synthesis
<220> FEATURE:
<221> NAME/KEY: BINDING
<222> LOCATION: 19
<223> OTHER INFORMATION: amino acid 19 (Cys) is attached by OH

<400> SEQUENCE: 5

Gly Leu Pro Trp Gly Cys Pro Ser Asp Ile Pro Gly Trp Asn Thr Pro
 1               5                  10                  15

Trp Ala Cys
```